United States Patent [19]

Simons

[11] Patent Number: 5,447,842
[45] Date of Patent: Sep. 5, 1995

[54] FETAL CELL RECOVERY METHOD

[75] Inventor: Malcolm J. Simons, Glenluce, Australia

[73] Assignee: GeneType A.G., Zug, Switzerland

[21] Appl. No.: 927,313

[22] PCT Filed: Mar. 27, 1991

[86] PCT No.: PCT/AU91/00115
§ 371 Date: Nov. 2, 1992
§ 102(e) Date: Nov. 2, 1992

[87] PCT Pub. No.: WO91/14768
PCT Pub. Date: Oct. 3, 1991

Related U.S. Application Data

[63] Continuation-in-part of Ser. No. 499,932, Mar. 27, 1990, Pat. No. 5,153,117.

[51] Int. Cl.[6] .......................... C12Q 1/24; C12Q 1/68
[52] U.S. Cl. ............................................. 435/6; 435/2;
435/7.21; 435/7.24; 435/7.25; 435/29; 435/30;
435/240.2; 435/240.21
[58] Field of Search .................... 435/2, 6, 7.21, 7.24,
435/7.25, 29, 30, 240.2

[56] References Cited

U.S. PATENT DOCUMENTS 4,675,286  6/1987  Calenoff ............................ 435/7.21
5,153,117 10/1992  Simons ..................................... 435/2

OTHER PUBLICATIONS

Samuel A. Latt, et al., "Methods In Cell Biology", vol. 26, 1982, pp. 277–295, Academic Press.
G. Michael Iverson, et al., "Prenatal Diagnosis", vol. 1, No. 1, 1981, pp. 61–73.
S. C. Yeoh, et al., "The Lancet", No. 2, Oct. 7, 1989, pp. 869–870.

*Primary Examiner*—David Saunders
*Attorney, Agent, or Firm*—Skjerven, Morrill, MacPherson, Franklin & Friel

[57] ABSTRACT

The present invention provides a method for selectively recovering fetal cells from a maternal blood sample. The method is performed on a blood sample from a pregnant woman having different first and second cell surface antigens expressed by a first allele of a polymorphic genetic locus and a second allele of a polymorphic genetic locus. The method separates maternal and fetal cells based on differential reactivities of the cells to antibodies specific for polymorphic cell surface antigens, particularly the HLA antigens. In particular, the fetal and maternal cells are separated based on the nonreactivity of the fetal cells to an antibody specific for a cell surface antigen encoded by a non-transmitted maternal allele. The method can be performed using solid phase-affixed antibody and recovering non-bound cells or using fluorescent labeled antibody and recovering unlabeled cells by fluorescence-activated cell sorting. In a preferred embodiment, the cells are also contacted with a second antibody specific for the second cell surface antigen. Fetal cells are separated based on their reaction with, at most, one of the antibodies.

26 Claims, No Drawings

FETAL CELL RECOVERY METHOD

This application is a continuation-in-part of Ser. No. 07/499,932, filed Mar. 27, 1990, now U.S. Pat. No. 5,153,117.

FIELD OF THE INVENTION

The present invention relates to a method for recovering fetal cells from maternal blood using antibodies to distinguish fetal cells having one maternal cell surface antigen for a polymorphic locus from maternal cells having both maternal cell surface antigens.

BACKGROUND OF THE INVENTION

The examination of fetal cells for early detection of fetal diseases and genetic abnormalities is undertaken in approximately one out of every thirty pregnant women. The main indication is maternal age (over 35 years). The tests may involve DNA gene typing or, more commonly, the use of live fetal cells for chromosomal karyotyping.

Fetal cells are usually obtained by amniocentesis, the removal of amniotic fluid from the amniotic cavity within the amniotic sac or placenta. The procedure presents a risk of harm to the fetus, particularly after the first trimester of pregnancy. The risk to the fetus together with the high cost of the procedure have prevented the establishment of examination of fetal cells for early detection of abnormalities as a routine procedure in pregnancy.

In the late 1970s and early 1980s, Herzenberg and his colleagues reported that fetal cells were present in maternal blood as early as 15 weeks gestation. The authors separated maternal and fetal cells using fluorescence-activated cell sorting (FACS) by staining maternal blood for a distinguishing paternal HLA antigen. The authors state that the demonstration that fetal cells enter maternal circulation and can be isolated by FACS-enrichment procedures could have practical significance in enabling karyotyping without the need for amniocentesis. The authors state that this would be possible if the frequency of successful isolation of cells at 15 weeks is sufficiently high and the cells could be induced to divide (enter metaphase). Furthermore, extensive HLA typing reagents, or other cell surface reagents would need to be developed to distinguish maternal and fetal cells. To date, the technique has not been successfully adapted for use as a clinical technique for either karyotyping or fetal DNA analysis.

Recently, fetal cells present in maternal blood have been used to perform analysis of genes present in the fetus. In one technique, the maternal and fetal cells were not separated and the DNA from the cell mixture was amplified with Y chromosome-specific primers to determine whether the fetus is male. It has been suggested that DNA amplification techniques can also be performed to detect gene sequences associated with disease in this manner. Of course, the method cannot be used where the mother is a carrier for the trait.

To date, amniotic fluid or chorionic villus biopsy has been the only source of antenatal cells to provide a sufficient number of live cells for karyotyping. Furthermore, DNA analysis methods have only been possible in relatively limited situations which depend on particular differences in maternal and fetal cells, e.g. presence of the Y chromosome in the fetus or presence of HLA-A2 antigen on fetal, but not maternal, cells.

DESCRIPTION OF THE PRIOR ART

Herzenberg and his colleagues have described methods for separating maternal and fetal cells in maternal blood using fluorescence-activated cell sorting (FACS). In Herzenberg et al, *Proc. Natl. Acad. Sci. USA* 76:1453–1455 (1979), cells in blood samples from 15-week pregnant HLA A2-negative women were stained for HLA A2 antigen. Stained cells were separated by FACS and collected to enrich the population of fetal cells. Although the technique was demonstrated to effectively identify male, HLA A2-positive cells in maternal blood, to date the technique has not been successfully adapted for general applicability. In Iverson et al, *Prenat. Diag.* 1:61–73 (1981), peripheral blood lymphocytes (PBLs) from either 15 week or 21 to 25 week pregnant women were examined. If the woman was HLA A2-negative, her cells were stained with anti-HLA A2 reagents, sorted by FACS onto microscope slides (for fetuses who were HLA A2-positive), stained with quinacrine and examined microscopically for Y chromatin-positive cells. The authors report that fetal cells enter the maternal circulation as early as 15 weeks gestation.

Bianchi et al, *Cytometry* 8:197–202 (1987) report a technique that allows direct hybridization to the DNA of cells which were flow sorted onto nitrocellulose filters which eliminates the need for a DNA isolation step. The method was performed on human cord blood. The authors state that the technique is useful in situations where there is a limited amount of DNA available for analysis such as for fetal cells recovered from maternal blood.

U.S. Pat. No. 4,675,286 (to Calenoff, issued Jun. 23, 1987) describes a method for obtaining fetal cells for diagnostic examination in which detached cells from the uterine cavity and outer surface of the amniotic sac are incubated with a separation antibody which binds preferentially to either fetal or maternal cells. The antibody can be bound to an insoluble support or conjugated with a fluorescent label and removed with a cell sorter to effect separation.

Truneh et al, *Cytometry* 8:562–567 (1987) describe a method for detection of very low receptor numbers on cells by flow cytometry. The method involves staining the cells with vesicles containing thousands of fluorochrome molecules, which vesicles are conjugated to antibodies with the desired specificity.

Albright et al, *Cytometry* 7:536–543 (1986) describe the use of centrifugal separation of cells in sputum specimens as an alternative to flow cytometry.

*Society for Clinical Cytology* 1988 Abstracts p.6 describe in situ hybridization for detection of structural and numerical abnormalities using nonradioactive probes for detection of aneuploidy and translocations (Pinkel et al, No. 13). The immunopotentiality of cancer patients was studied by sorting peripheral blood T cell subsets by a multiparameter analysis using monoclonal antibodies and flow cytometry (Nonura et al, No. 14).

*Practical Flow Cytometry (Second Edition)* by Howard M. Shapiro, Alan R. Liss, Inc. 1988 is a comprehensive work on flow cytometry. The book describes how to build, purchase and use a flow cytometer and how to design analyses and analyze the data produced thereby.

Each of the above-described references and the references cited therein is incorporated herein by reference in its entirety.

SUMMARY OF THE INVENTION

The present invention provides a method for selectively recovering fetal cells from a maternal blood sample. The method is performed on a blood sample from a pregnant woman having different first and second cell surface antigens expressed by a first allele of a polymorphic genetic locus and a second allele of a polymorphic genetic locus. The method separates maternal and fetal cells based on differential reactivities of the cells to antibodies specific for polymorphic cell surface antigens, particularly the HLA antigens. In particular, the fetal and maternal cells are separated based on the non-reactivity of the fetal cells to an antibody specific for a cell surface antigen encoded by a nontransmitted maternal allele.

The method comprises the following steps. Cells from a blood sample of a pregnant woman having a first cell surface antigen encoded by a first allele of a polymorphic genetic locus and a second, different cell surface antigen encoded by a second allele of a polymorphic genetic locus are combined with an antibody specific for the first cell surface antigen for a period of time sufficient for antibody binding. Cells bound to the antibody are separated from any cells which are not bound to the antibody and non-bound, separated cells are recovered. Fifty percent of the time, the allege encoding the antigen is not transmitted and maternal cells bound to the antibody can be separated from non-bound fetal cells.

In a preferred embodiment, the cells are also contacted with a second antibody specific for the second cell surface antigen. The maternal cells react with both antibodies. Except when the fetus inherits both maternal alleles, fetal cells react with, at most, one of the antibodies. In a most preferred embodiment, the alleles are for a single genetic locus, preferably an HLA locus. In this way when the fetus does not inherit the nontransmitted allele from the father, the fetal cells, having inherited only one of the two maternal alleles, react with only one of the two antibodies. In instances where the fetus is the same HLA type as the mother for those alleles (i.e., where the fetus inherits the non-maternally transmitted allele from the father), there will be no difference between the reactivity of the fetal and maternal cells with the antibodies. Antibodies specific for another maternal HLA antigen can be used until cells in the sample fail to react with one of the antibodies.

The differential antibody reactivities of the fetal and maternal cells can be used to separate the cells in two general ways based on affixing the antibodies to a solid phase or based on FACS using fluorochrome-labeled antibodies. For solid phase separations, the cells are separately contacted with solid phase-affixed antibodies for each selected maternal antigen (e.g., magnetic bead-affixed antibodies). Maternal cells bind to each antibody. Fetal cells fail to react with antibodies for nontransmitted antigens, are not bound to the solid phase, and are recovered. For FACS-based separations, the antibodies are labeled with a fluorochrome, and unlabeled fetal cells are separated from labeled maternal cells. In a preferred embodiment, antibodies for two maternal alleles are labeled with different fluorochromes and double-labeled maternal cells are separated from unlabeled and single-labeled fetal cells.

The separated fetal cells can be used in a variety of procedures. The DNA in the recovered fetal cells can be used to determine a variety of genetic traits, particularly using DNA amplification methods. In a preferred embodiment, the fetal cells are cultured and the cultures used for karyotyping. It is also envisaged that cytogenetic abnormalities classically revealed by karyotyping and by in situ hybridization may also be revealed by gel electrophoresis.

DETAILED DESCRIPTION OF THE INVENTION

The present invention provides a method for selectively recovering fetal cells in a maternal blood sample. The method is based on separating maternal and fetal cells based on differential reactivities of the cells to antibodies specific for polymorphic surface antigens of the cells, particularly the HLA antigens. For HLA loci (or any other polymorphic genetic loci), the fetus inherits one allele for an HLA locus from the mother. The non-reactivity of fetal cells with an antibody specific for the antigen expressed by the nontransmitted allele can be used to separate fetal and maternal cells.

Specifically, an antibody for the selected maternal antigen can be affixed to a solid phase. Maternal cells become solid-phase affixed by reaction with the antibody. When the antigen is encoded by the nontransmitted allele (and the fetus does not inherit the nontransmitted maternal allele from the father), fetal cells do not bind to the antibody and can be recovered. Alternatively, the antibody can be labeled with a fluorochrome and labeled maternal cells separated from any unlabeled fetal cells.

Preferably, antibodies specific for two maternal cell surface antigens are used. When two selected maternal alleles are for different polymorphic genetic loci, there is a one in four chance that the fetus will inherit both alleles. That is, three out of four times, the fetus will inherit either one or neither of the two maternal alleles from the mother. Therefore, when a maternal blood sample is combined with antibodies for each selected allele of those HLA loci (and the fetus does not inherit the nontransmitted maternal allele from the father), the maternal cells react with both antibodies and the fetal cells react with one antibody (two out of four times) or neither antibody (one out of four times).

When the mother is heterozygous for an HLA locus (and the fetus does not inherit the nontransmitted maternal allele from the father), the mother and fetus have different alleles for that HLA locus. Therefore, when a maternal blood sample is combined with antibodies, maternal cells react with both antibodies and fetal cells react with only one of the antibodies.

When the antibodies for two maternal antigens are labeled with different fluorochromes, single-labeled and unlabeled fetal cells are readily separated from double-labeled maternal cells using fluorescence-activated cell sorting (FACS), resulting in separation and recovery of fetal cells. Similarly, when antibodies for a cell-surface antigen encoded by a nontransmitted maternal allele are bound to a solid phase, such as a magnetic bead, only maternal cells bind to the solid phase. The non-bound fetal cells can be readily separated from the bound maternal cells and recovered.

The recovered fetal cells can be used in a variety of assays. The DNA in the recovered fetal cells can be used to determine a variety of genetic traits. In a preferred embodiment, the fetal cells are cultured and the cultures used for karyotyping. It is also envisaged that cytogenetic abnormalities classically revealed by karyotyping and by in situ hybridization may also be revealed by gel electrophoresis.

The present fetal cell recovery method provides advantages which could not be achieved in prior art methods. The most significant difference from prior art methods is that no information regarding the paternal contribution is necessary. Only maternal HLA alleles need to be identified. Not only is there no need to identify alleles of the natural father that may be distinguishing, but, so long as the fetus does not inherit nontransmitted maternal alleles from the father, only a limited number of antigens need be investigated to find a pattern that distinguishes maternal and fetal cells.

There is also no need to use a mixture of antibodies specific for all non-maternal allele-encoded antigens for the selected loci. The method does not rely on attempting to identify fetal cells with discriminating paternal alleles that the child may have inherited. Furthermore, since the method separates fetal and maternal cells based on absence of the maternal antigen in fetal cells, fetal cells can be effectively separated even if the paternal antigen had never been previously encountered. Once antigens present on the maternal cells are identified, any of the nontransmitted antigens can form the basis of the separation. Furthermore, the presence of cells in the sample which do not react with one of the antibodies indicates that the fetal cells have been distinguished based on differential antibody reactivity. No additional evaluation needs to be made.

The method also does not attempt to distinguish the fetal cells based on "fetal" antigens such as fetal hemoglobin which may also be expressed by some maternal cells. In the present method, rather than selecting a fetal antigen that is present on some maternal cells (oncofetal antigens), the method utilizes a maternal antigen which is not present on any fetal cells. Once an antibody that does not react with some cells in the sample is identified, all of the cells which do not react with the antibody are fetal cells. Furthermore, all nucleated fetal cells that express HLA antigens fail to react with the antibody because the HLA antigen is not transmitted to that fetus. The lack of reactivity is not related to a particular fetal stage of development or to a particular fetal cell type. Therefore all non-reactive cells are fetal cells.

Selection of Polymorphic Genetic Locus-Encoded Antigens

The fetus inherits half of its chromosomes from its mother and half from its father. For each polymorphic locus, such as an HLA locus, the fetus inherits one allele from its mother and one from its father. Therefore, the mother and fetus always have at least one allele for each polymorphic locus in common. The maternal alleles that the fetus does not inherit are unique to the maternal cells except when the fetus inherits the nontransmitted allele from the father.

For any polymorphic loci, the fetus will inherit at most one of the maternal alleles. When the mother is heterozygous for the locus, the mother and fetus will have the same alleles only when the fetus inherits the nontransmitted allele from the father. The likelihood of that event depends on the frequency of the nontransmitted allele in the population. Loci are preferably selected to minimize the likelihood that the fetus inherited the allele for the selected antigen from the father as described below.

Numerous polymorphic loci are well known, as are methods for determining allele-types for those loci directly or indirectly by determining the cell surface antigens expressed by the loci. The selected loci have at least two alleles each of which comprises a significant percentage of the population. Preferably, the loci have numerous alleles which are present in a significant percentage of the population. Selection of such loci maximizes the likelihood that the father will not provide the nontransmitted maternal allele to the fetus.

In a preferred embodiment, the selected alleles of the loci are routinely detected using serological methods. In this way, the antibody reagents available to type the loci are then available for use as reagents in the separation method of this invention.

Suitable loci encode cell surface antigens present on cells in early through late stages of differentiation. However, any surface antigens expressed by nucleated fetal cells can be used. Exemplary suitable genetic loci encode the blood group antigens, particularly the ABO group, the Kidd group, the Duffy group, the Lewis group, the P group, the I group, and like groups. Polymorphic loci which would provide equivalent results are those associated with the minor histocompatibility antigen loci and any other polymorphic loci that encode cell surface antigens present on fetal and maternal cells. Most preferred genetic loci for use in the method are the HLA loci. The antigens are expressed by all nucleated cells and are present on fetal cells early in development. Furthermore, methods for determining the HLA type of an individual are well known and numerous antibodies for HLA antigens are commercially available. The remainder of the discussion of selection of antigens will use the HLA antigens as exemplary. Similar considerations apply to use of antigens encoded by other polymorphic genetic loci.

For the present method, if the maternal HLA type is known, any HLA antigen-specific antibodies that are available for any two maternal HLA antigens can be used. Preferably the antibodies are specific for the antigens of any HLA locus at which the mother is heterozygous.

When the maternal HLA type is unknown, the alleles for at least one HLA locus, preferably two or more loci, are determined, preferably by using antibodies specific for antigens of that locus. When antibodies specific for two alleles of a locus react with the maternal cells, those antibodies can be used to identify and separate fetal cells. In this way, it is clear at the outset of the separation procedure that antibody reagents useful in the method are available. Alternatively, the HLA type can be determined by DNA methods and an allele can be selected based on availability of antibodies for the encoded antigen.

Preferably, the loci are any two of the Class I loci (A, B, and C) and the Class II (DR, DQ and DP) loci. Since those loci are commonly typed by serological methods, HLA antigen-specific antibodies for many alleles of those loci are commercially available. In particular, there are numerous monoclonal antibodies for A and DR/DQ antigens.

In selecting the HLA alleles to use, the first consideration is the availability of antibodies for the antigens expressed by the alleles. When antibodies for the antigens of a number of alleles present in the mother are available, preferably, the alleles chosen are from a locus that has numerous alleles present in significant numbers in the population, as described above.

Antibodies specific for the antigen of any of the alleles of maternal HLA loci can be selected for use in separating cells of the maternal blood sample. The antibodies can be polyclonal or monoclonal, preferably monoclonal. The selected alleles can be for two different loci.

When the alleles for two HLA loci are used, the fetus will only inherit both alleles if the alleles are on one chromosome and recombination has not occurred. In that case, the use of two loci will have the same result as use of a single locus. That is, half of the time the selection results in an effective separation and half of the time, the fetus has the same alleles as the mother and no separation is achieved. To ensure separation using two alleles, the selected alleles must be from different chromosomes; i.e., that is from different maternal haplotypes.

Most DNA methods and all serologic methods do not determine the haplotype of the mother. For two genetic loci, four allele types are determined, but no information as to the alleles that comprise a haplotype is determined. For the present method, it is preferred that the haplotype is determined to ensure that the selected alleles are not inherited together. Methods for determining haplotypes include analysis of haploid cells (exemplified by analysis of DNA in sperm) and a method where DNA is diluted to haploid (Ruano et al, *Proc. Natl. Acad. Sci USA*, 87:6296–6300 (1990)). A preferred method is described in EPO application Serial No. 90.309107.2, filed 8/20/90 entitled *Intron Sequence Analysis Method for Detection of Adjacent and Remote Locus Alleles as Haplotypes* by Malcolm J. Simons, published Feb. 25, 1991.

Alternatively, if both maternal alleles for a single genetic locus are determined, the alleles are necessarily present on different chromosomes and the fetus inherits one and only one of the alleles from the mother. Therefore, whenever appropriate reagents are available, antibodies specific for two antigens encoded by alleles of a single genetic locus are selected.

As stated previously, the antibodies are preferably specific for the two antigens expressed by the alleles of one HLA locus. In another preferred embodiment, the antibodies are specific for both antigens expressed by the alleles of more than one HLA locus. When the fetus inherits the nontransmitted maternal allele(s) from the father, the separation process is repeated selecting antibodies to antigens produced by the alleles of another HLA locus or loci. Similar considerations apply for selection of antigens encoded by other polymorphic genetic loci.

Once the antibodies for use for a particular sample are selected, the antibodies are either bound to a solid phase or used to label the cells, depending on the type of separation procedure. Each of the procedures is described generally below. In addition, an exemplary preferred procedure for each type of separation method is described in detail in the Examples.

Source and Purification of Cells

The present method is designed to recover fetal cells present in a maternal blood sample, particularly a venous blood sample. Preferably, the pregnant woman is in her first trimester of pregnancy. The sample can be any blood sample which is prevented from clotting such as a sample containing heparin or, preferably, ACD solution. The sample is preferably stored at 0° to 4° C. until use to minimize the number of dead cells, cell debris and cell clumps. The number of fetal cells in the sample varies depending on factors including the age of the fetus, number of fetal/maternal bleeds, the volume of blood in each episode, and the amount of time since the last bleed. Typically, from 7 to 20 ml of maternal blood provides sufficient fetal cells upon separation from maternal cells. Preferably, 30 ml or more blood is drawn to ensure sufficient cells without the need to draw an additional sample. When a second separation is necessary, cells can be incubated at 37° C. for about 2 hours, then washed to remove previously used antibodies. Additional blood samples are not required.

Maternal blood contains at least three main types of nucleated fetal cells: nucleated erythroid cells, syncytiotrophoblasts and lymphoid cells. Blood samples are purified to eliminate red blood cells (RBCs). Preferably, the three main types of nucleated fetal cells are maintained in the purified sample. RBCs can be eliminated by incubating the cells in a hypotonic solution, e.g., 0.87% ammonium chloride with 0.037% EDTA. This procedure is particularly preferred for solid phase-based separations since density gradient materials such as Ficoll can coat the cells with sugar which interferes with the separation process.

Alternatively, peripheral blood lymphoid cells (PBLs) harvested by density gradient separation can be used. PBLs comprise the majority of the nucleated fetal cells. To purify PBLs, conveniently, a density gradient medium having a density intermediate between the densities of RBCs and PBLs such as Ficoll-Hypaque and Percoll (both from Pharmacia, Piscataway, N.J.) is used to harvest the PBLs. The layer of PBLs is removed and resuspended in a suspension medium. The cells are washed and the pellet is resuspended in the suspension medium at an appropriate concentration for the separation procedure. Similarly, specific banding materials for density gradient separation of nucleated erythroid cells and syncytiotrophoblasts can be utilized.

Solid phase separation methods are discussed below, followed by discussion of FACS separations. Suspension media and appropriate cell concentrations for solid phase-based and FACS-based separation procedures are described in those discussions.

Solid Phase Separation

As stated previously, fetal cells can be separated from maternal cells in blood based on the lack of reactivity of the fetal cells with an antibody specific for a nontransmitted maternal cell-surface antigen. Briefly, the maternal antigen-specific antibody can be bound to the solid phase directly or through use of a solid phase-affixed bridge which binds the antigen-specific antibody. Maternal cells bind to the bridge and are affixed to the solid phase. When the antigen-specific antibody is for the antigen of the nontransmitted allele, fetal cells do not bind to the solid phase and can be separated and recovered. Separation procedures are described below.

Selection and Preparation of Solid Phase for Separation

The solid phase for separating fetal cells can be those used conventionally for antibody-based cell separations, such as plastic plates, dishes, flasks, and tubes; beads, e.g., polyacrylamide, Sephadex, agarose-polyacrolein, trisacryl and latex; nylon disks and ox red blood cells. The solid phase can be in the form of a dish, flask or tube with which the cells are contacted, present as beads or disks in a container or packed into a column (e.g., beads and red blood cells) through which the cells are passed. Most preferred is use of magnetic beads present in a tube or other container. Affinity chromatography methods for cell isolation are well known and are described in *Affinity Chromatography: A Practical Approach*, ed. P.D.G. Dean, IRL Press (1985) and the references cited therein, each of which is incorporated herein by reference in its entirety.

The antibody can be bound to the selected solid phase by conventional processes for the solid phase materials including adsorption, ionic bonding, van der Waals adsorption, electrostatic bonding, or other non-covalent or covalent bonding. Procedures for non-covalent bonding are described in U.S. Pat. No. 4,528,267. Procedures for covalently bonding antibody solid supports are described by Ichiro Chibata in IMMOBILIZED ENZYMES. Halsted Press: New York (1978) and A. Cuatrecasas, *J. Bio. Chem.* 245:3059 (1970), the entire contents of which are hereby incorporated by reference.

The antibody can be bound to the solid phase either directly or indirectly such as through the use of a surface layer to which the antibody is attached. For example, the surface can be coated with a protein and the protein coupled with the antibody using a coupling agent (for example, glutaraldehyde). The antibody can be bound by applying the antibody in aqueous solution to a surface coated with a layer having free isocyanate groups (such as a polyether isocyanate). Additionally, the antibody can be coupled to a hydroxylated material by means of cyanogen bromide.

Alternatively, an antibody "bridge" can be bound to the solid phase and used to indirectly bind the anti-maternal antigen antibody either prior to or during the separation procedure. Bridges include antibodies which are specific for immunoglobulin of the species of the anti-maternal antigen antibody, also referred to a second antibody. For mouse monoclonal antibodies, exemplary bridge antibodies are goat anti-mouse immunoglobulin, goat anti-mouse IgG and goat anti-mouse IgM. Other bridges include use of staph protein A (SPA) (which binds the Fc region of immunoglobulin) or use of avidin to bind biotinylated antibodies. When applicable, specialized methods for binding antibodies to a particular type of solid phase are described below. Many solid phase-based cell separations are generally performed by reacting the specific antibody with the cells and then reacting the cells with solid phase-affixed second antibody or other bridge.

For solid phase applications, following binding of the antibody, the solid phase can be "blocked" to reduce non-specific binding such as by use of water-soluble, non-immune animal proteins including albumins, casein and non-fat milk.

In a preferred solid phase separation method, the antibody is affixed to a metal or magnetic bead and combined with the cells in a tube or other container. Following binding, solid phase-affixed maternal cells are removed from the cell suspension medium using a magnet. Beads which are attracted by a magnet are commercially available. A preferred bead is sold by Dynal AS under the name DYNABEAD (available from Robbins Scientific of Mountain View, Calif.). Antibodies can be conjugated to the beads according to the manufacturer's directions. In addition, beads having goat anti-mouse IgG antibodies conjugated to the surface are available. Any mouse monoclonal IgG antibody can be readily bound to the bead by incubation with the bead in a physiologic solution. A tube holder containing a magnet to which the DYNABEAD beads are attracted is also available from Dynal AS.

For a column separation, the column packing materials must have appropriate spacing so that maternal cells can react with an antibody affixed to the column materials and fetal cells which do not have the antigen can pass through the column. Column materials which are suitable for use in separating cells include various types of beads and ox red blood cells.

Similarly, an antibody for the selected maternal antigen can be affixed to a solid phase such as a microtiter plate, a culture dish, a test tube, a centrifuge tube or like suitable containers for cells. Non-bound fetal cells can be separated from maternal cells and removed by gently washing the surface of the solid phase. Solid phase materials which are suitable for affinity separation of cells are well known and are commercially available.

As stated above, for each type of the solid phase the antibodies can either be affixed to the solid phase or bound to the solid phase by reaction with a solid phase-affixed bridge. Additional alternative embodiments which provide the same result can be readily envisaged by one of ordinary skill.

Preparation of Cells suspension media and appropriate cell concentrations for solid phase-based separation procedures can be those used conventionally for solid phase-affixed, antibody-based cell separations. The suspension medium can be any physiologic medium compatible with antibody function and with preservation of the fetal and maternal cells; e.g., physiologic saline, phosphate buffered saline and like solutions used for immunoassay procedures. The suspension medium can also be a tissue culture medium which optimizes the ability to culture recovered cells. Suitable tissue culture media are described in the description of suspension media for FACS separation methods. The suspension medium can additionally contain antibiotics, and like additives commonly present in tissue culture media. The suspension medium should be free from reagents which can interfere with subsequent use of the separated cells. For example, preservatives are preferably not used if the cells are to be cultured following separation.

For separations using bead-affixed antibody, the suspension medium is preferably calcium- and magnesium-free to minimize monocyte activity and thus decrease the tendency of the monocytes to engulf the beads during the separation process. In addition, the medium may contain an anticoagulant such as heparin or ACD.

Solid phase separation procedures are performed in a relatively short period of time, so that use of PBS is sufficient to maintain cell viability throughout the separation procedure. However, the cells are preferably resuspended in a tissue culture medium following separation for uses involving culture of the cells.

Following purification of the blood sample, if any, the cells are washed and the pellet is resuspended in the selected suspension medium at an appropriate concentration for solid phase separations. Generally, those concentrations range from about $10^5$ to about $10^8$ cells/ml, preferably about $10^6$ to about $10^7$ cells/ml.

The cell suspension is contacted with the solid phase-affixed antibody as described hereinafter.

Solid Phase Separation Process

To effect the separation, cells of the sample are combined with a solid phase-affixed antibody specific for one of the selected maternal antigens for a time sufficient for antibody binding. The period of time varies depending on the temperature and is well known. Incubations of as little as one minute at room temperature are adequate. Longer periods may be required at 4° C. More important is that there is sufficient time for the cell surface antigen to come into contact with the solid phase-affixed antibody. Usually times of from about 10 to about 60 minutes are sufficient.

The cells bound by the maternal antigen-specific antibody (and thus to the solid phase) are separated from cells which are not bound to the solid phase. When there are cells in the sample which are not bound by the selected antibody, those cells are recovered. When all cells in the sample are bound by the first antibody, the procedure is repeated using an antibody for the second selected maternal cell surface antigen and non-bound, separated cells are recovered. The separations using the first and second antibodies can be performed sequentially. Preferably, the separations are separately performed at substantially the same time using different aliquots of the sample cells.

For bead separations, maternal cells always bind to the bead. Fetal cells do not bind when the solid phase-affixed antibody is for a nontransmitted maternal antigen. The cells in the sample can be divided and an aliquot of cells can be combined separately with beads containing antibody specific for each of the selected maternal antigens simultaneously. Fetal cells do not bind to one of the sets of beads, if the nontransmitted allele was not inherited from the father. Solid phase-affixed maternal cells are separated from non-bound fetal cells by separating the beads from the suspension medium.

For magnetic beads, the cells are incubated with the beads for about an hour, preferably at 4° C. The incubation is preferably not more than about an hour to avoid clumping by monocytes. The beads are present in the incubation at about $10^6$ to $10^7$ beads/ml. A preferred cell to bead ratio is about 2 beads/cell. Following incubation, maternal cells affixed to the beads are moved to the side of the tube in which the incubation is performed using a magnet and non-bound fetal cells are removed by gentle washing. The final wash medium preferably contains not more than 1% protein.

For column-based separations, the method is accomplished by passing an aliquot of the sample through the column at a flow rate sufficient to permit antibody binding. Fetal cells pass through the column when the solid phase-affixed antibody is for a nontransmitted maternal antigen. The cells in the sample can be divided and an aliquot of cells can be passed through a column containing antibody specific for each of the selected maternal antigens simultaneously. Fetal cells elute from one of the columns, if the nontransmitted allele was not inherited from the father.

Alternatively, cells can be passed through one column and, when no fetal cells elute, either cells can be removed from the column and passed through another column or a second aliquot of cells can be passed through a column for the second maternal antigen. Cells can be separated from column materials or other solid phase surfaces using an excess of the maternal antigen or a competitive inhibitor for the antibody binding site, by mechanical disruption (e.g., pipetting), or, for ox red blood cells, by lysis of the erythrocytes. Additional techniques for removing cells affixed to particular surfaces are well known and include cleavage of particular bonds used to attach the antibody to the solid phase; e.g. cleavage of disulfide bonds with thiol. Preferably, separate aliquots of the cells are used so that fetal cells having the selected maternal antigen need not be separated from the solid phase.

For separations using containers such as plates or tubes, the cells are incubated with the solid phase-affixed antibody for a time sufficient for antibody binding. Following incubation, any non-bound cells are gently washed from the surface and recovered.

FACS Separation

The fetal cells can also be separated from maternal cells in blood based on the differential labeling of the cells and separation of the labeled cells using FACS. Briefly, as stated previously, the maternal cells can be labeled with an antibody for a selected maternal antigen. In that case, fifty percent of the time, the sample will contain unlabeled fetal cells. Preferably, the maternal cells are double-labeled. When the selected maternal antigens are encoded by alleles of different genetic loci, three out of four times, fetal cells are unlabeled or single-labeled depending on whether the fetus inherits one or neither of the maternal alleles. When the selected maternal antigens are encoded by alleles of the same genetic locus, fetal cells are single-labeled. The separation procedure is described below using double labeled maternal cells as exemplary.

Preparation of Cells

Suspension media and appropriate cell concentrations for FACS-based separation procedures are those conventionally used. Following purification, if any, the cells are washed and the pellet is resuspended in the suspension medium at an appropriate concentration for sorting. The concentration should not be too dilute. However, the flow cytometer can be adjusted to provide an appropriate cell flow rate using relatively concentrated or relatively diluted samples. Preferably the cell concentration is from about $10^6$ to about $5\times10^8$, more preferably from about $5\times10^6$ to about $1\times10^7$ cells/ml.

The suspension medium is a physiologic solution, such as a physiologic buffer, to maintain cell integrity. Most physiologic buffers, e.g. Tris buffer, phosphate buffer (PB), citrate buffer, phosphate buffered saline (PBS) are suitable. Balanced salt solutions such as Earle's balanced salt solution (EBSS), Hank's balanced salt solution (HBSS), and Gey's balanced salt solution (GBSS) are also suitable. Preferably, the suspension medium is a tissue culture medium (e.g., basal medium Eagle and Dulbecco's modified Eagle's medium), more preferably an enriched tissue culture medium suitable for use with lymphocyte cultures such as RPMI 1640. The use of a tissue culture medium, particularly a medium adapted for the growth of the sample cell type, provides an environment which maximizes cell stability.

The suspension medium can additionally be supplemented with a protein source at a relatively high concentration. The protein source can be albumin such as bovine serum albumin (BSA) or, preferably, human serum albumin (HSA) at a concentration in the range of from about 5 to about 10%. Alternatively, the protein source can be serum such as fetal calf serum or human serum at a concentration of from about 5 to about 10%. Since lymphocytes can be stimulated by the presence of foreign antigens, preferably the protein source is human. Most preferred is the use of about 5% autologous plasma which can be harvested from the purified blood sample and is nonimmunogenic.

Alternatively, the protein source can be added to the flow cytometer collection vessel, rather than to the suspension medium, to cushion the fall of the cell into the vessel, enhancing cell stability.

Labeling the Cells

The cells of the blood sample, preferably purified cells, are labeled with fluorescent antibodies specific for the antigens encoded by at least one maternal polymorphic locus, selected as described previously. The antibodies can be polyclonal or monoclonal, preferably monoclonal. Preparation of polyclonal and monoclonal antibodies for an antigen of interest is well known.

For HLA antigens, as stated previously, HLA antigen-specific antibodies are commercially available. Typically the HLA Class I loci (A, B and C) and the Class II DR and DQ loci are determined by serological methods. Therefore, antibodies specific for those antigens are readily available. Sources of HLA antigen-specific antibodies include Genetic Systems (Seattle, Wash.) and C6 Diagnostics (Mequon, Wis.). Blood group antigens are also determined serologically and the antibodies are commercially available.

The antibody is labeled with a dye that facilitates, cell sorting, particularly a fluorochrome. Suitable dyes for FACS analysis and/or separation are well known. Those dyes are described in *Practical Flow Cytometry* (*Second Edition*) by Howard M. Shapiro, supra, at pages 115-198. Preferred dyes are fluorochromes including fluorescein (e.g., fluorescein isothiocyanate—FITC), rhodamine (e.g., tetramethylrhodamine isothiocyanate—TRITC), phycoerythrin (PE), allophycocyanin (APC) and Texas Red (Molecular Probes, Eugene, Oreg.). The combinations of fluorochromes used for labeling are chosen so that distinguishable wavelengths of light are emitted. A preferred combination is a fluorochrome that emits green light together with one that emits red or orange light, e.g., FITC with PE or Texas red.

For those flow cytometers that can perform a four-color sort, the cells can be labeled with antibodies for antigens expressed by four alleles. In that case, preferably, the antibodies are specific for both antigens expressed by the alleles of two maternal HLA loci. Maternal cells are labeled with all four fluorochromes. Fetal cells are labeled with two of the four fluorochromes when none of the nontransmitted maternal alleles is inherited from the father. By using four fluorochromes from two loci, the fetal cells remain distinguishable from the maternal cells even when the fetus inherits one of the nontransmitted maternal alleles from the father. A second staining is only necessary when the fetus inherits both nontransmitted maternal alleles from the father. When the antibodies are for antigens expressed by three or four maternal loci, using the additional dyes increases the likelihood that the fetus did not inherit each of the maternal alleles.

Fetal cells are only indistinguishable from maternal cells by the method of the present invention in the case where the fetus inherits all six nontransmitted maternal alleles from the father.

The antibody can be labeled with the fluorochrome, directly or indirectly, by well known methods. The conjugation methods for attaching labels to antibodies generally can be used for these purposes. Direct labeling methods for dyes such as FITC are described in Catty et al, in "Antisera in Immunoassays with Special Reference to Monoclonal Antibodies to Human Immunoglobulins", *IMMUNOASSAYS FOR THE 80's*, supra, pp 133-153 and *THE HANDBOOK OF EXPERIMENTAL IMMUNOLOGY* 4th Edition, Vol. 1: Immunocytochemistry, ed. D. M. Weir, Blackwell Scientific Publications and in the publications cited in those references. The entire contents of each of those references is hereby incorporated by reference.

Preferably the labeled antibody is purified to remove unbound label prior to use. Preferably, the procedure used also purifies the antibody composition to provide the immunoglobulin fraction, more preferably, to provide the IgG fraction for polyclonal antibodies or, for monoclonal antibodies, the IgG or IgM fraction depending on the isotype of the antibody. Procedures for isolating the antibody fraction of an antibody include the use of recombinant protein G for IgG and immunoprecipitation for IgM. Procedures that additionally separate unbound fluorochrome are well known and include use of a DEAE G 35 sephadex (Pharmacia) column. Exemplary purification procedures are described in detail in the examples.

For dyes such as PE which are more difficult to attach while maintaining antibody activity, the antibody can be labeled with biotin. The dye can be attached by incubation of the biotinylated antibody with PE-avidin or PE-strepavidin (which are commercially available) either concurrently with or, preferably, following incubation of the antibody with the cells. A procedure for conjugating biotin to an antibody is described in Edward A. Bayer et al, "The Avidin-Biotin Complex in Affinity Cytochemistry", in *METHODS IN ENZYMOLOGY* Vol. 62 (1979) That article is incorporated herein by reference in its entirety.

An exemplary preferred direct labeling method for FITC is described in detail in the examples. A preferred indirect labeling method for biotinylation of an antibody and attachment of PE-strepavidin is also described.

To label the cells with the labeled, HLA antigen-specific antibodies, the cells are incubated with the antibodies for a time sufficient for substantially complete antibody binding under the conditions used. An excess amount of antibody is preferably used. A concentration of about 2 $\mu$g for $10^6$ cells is desirable. However, use of 50 $\mu$l of purified antibody at a concentration of about 40 $\mu$g/$\mu$l was sufficient.

The cells are preferably incubated at about 4° C. to maintain cell integrity. Incubation for about 30 minutes at 4° C. is usually sufficient for substantially complete antibody binding. The sample is preferably mixed, as by using a hematology blood rocking device, during the incubation to ensure contact of the antibodies with the cells. Preferably, the incubation is performed in the dark when using a fluorochrome label. Secondary reactions (e.g. incubation of fluorochrome-labeled avidin with biotin-labeled cells) are performed in the same manner.

Exemplary preferred cell labeling procedures for direct and indirect labels are described in detail in the examples.

Sorting Labeled Cells

Flow cytometry is a process in which the measurement of physical and/or chemical characteristics is made while the cells or particles pass, usually individually, through a measuring apparatus in a fluid stream. Biological particles, usually cells, have been subjected to flow cytometric analysis using acoustic, nuclear radiation, electronic and optical sensors. Optical measurements are used for the widest range of applications.

Most of the present applications of flow cytometers derive from the ability of the apparatus to define and quantify heterogeneous cell populations. Physical and chemical characteristics or parameters of cells which can be measured by flow cytometry include cell size, cell shape, pigment content, protein content, DNA content and DNA base ratio. In addition, cells can be labeled with one or more fluorochrome(s) and characterized based on color differences.

The most demanding applications of flow cytometry require identification and subsequent characterization of subpopulations of cells. Both flow sorting and multiparameter analysis are used for this purpose.

Flow sorting employs electrical and/or mechanical means to divert cells with preselected characteristics from the main stream, and can be used to isolate pure populations of viable cells with more homogeneous characteristics than could be obtained by any other means. Flow sorting is particularly useful in circumstances in which further characterization of the selected cells requires short- or long-term maintenance in culture or analytical procedures which cannot be accomplished by flow cytometry.

The parameters which can be used to sort cells include measurements of light scattered by cells at two different angles (less than 2°, commonly called forward scatter, and about 90°) from an incident laser beam. The fluorescence measurement capability of a multiparameter flow cytometer incorporating the light scattering measurements can then be used to determine other characteristics of the individual cell subpopulations.

For samples containing substantially larger numbers of fetal cells, the cells can be selected by a one or two step separation procedure by binding the cells to solid phase-affixed anti-maternal HLA antigen antibodies. For example, maternal cells and fetal cells bind to a column or other solid phase (such as a tissue culture dish surface or magnetic beads) with the shared maternal antigen antibody. Only maternal cells bind to a column (or other solid phase) having antibody to the antigen the fetus did not inherit. In this way, the fetal cells are separated from the maternal cells when incubated with the antibody to the antigen the fetus did not inherit.

For purposes of the present method, the cells are sorted using the four color patterns produced by differential staining with two fluorochromes as a selection criteria. When using red and green fluorochromes, the four patterns are (1) unstained, (2) red only, (3) green only and (4) red and green.

Following staining or labeling of the cells with a red and a green fluorochrome for each of the two maternal alleles, maternal cells are red and green. Fetal cells are either red or green, depending on the allele the fetus inherited. By selecting cells exhibiting either red or green fluorescence, but not both, the fetal cells can be isolated.

Since most flow cytometers can sort on three parameters, an additional selection criteria can be cell size. This criteria eliminates dead cells, debris and cell clumps. However, when the sample is carefully manipulated and kept refrigerated, dead cells do not appear to be a problem.

In a preferred embodiment, an additional selection criteria is DNA content. Fetal cells having greater than 2C DNA content can be determined using a number of vital-staining fluorochromes such as the Hoechst dyes, DAPI (4'-6-diamidino-2-phenylindole), hydroethidine and 7-aminoactinomycin D (7AMD). The fluorochrome used depends on the labels used to select the fetal cells. A second laser capable of emitting UV light is required to excite Hoechst and DAPI dyes. Each of the above-described dyes can be used with FITC and PE.

A flow cytometer can process about $10^7$ to $10^8$ cells per hour, usually about $4 \times 10^7$ cells per hour. Typically, the sample prepared from about 20 ml of maternal blood includes at least about $2 \times 10^8$ cells which can be sorted in about 5 hours to provide sufficient fetal cells for analysis. However, substantially fewer cells may be required, depending on the analysis method to be used.

The ability of the cell sorter to separate maternal and fetal cells ultimately depends on the percentage of fetal cells in the sample. To obtain a fetal cell sample that is at least about 60% pure (60% of the sorted cells are fetal cells), the fetal cells must constitute about 0.001% of the maternal cells or greater. Preferably, the sample contains 80%, more preferably 90% fetal cells post-sorting.

When 100% purity is desired, the sorted cells can be micromanipulated. For example, cell suspensions containing an individual cell per a preselected volume of suspension medium can be prepared by limiting dilution. Drops containing individual cells can placed in suitable containers (e.g. 96 well plates) and examined visually with a fluorescent microscope to identify single-labeled (or unlabeled) cells. Wells containing those cells can be marked and the cells pooled.

For PCR analysis, analysis can be performed using a single, unambiguously identified fetal cell. For karyotyping, the analysis can be performed using as few as five cells in metaphase. The number of cells necessary to obtain 5 metaphase cells will vary depending on the method used to induce metaphase and the length of culture required. For cells selected to have 2 C or greater DNA, a substantially shortened culture period may be used.

Alternatively, ways can be envisaged of identifying monozygosity (indicative of the presence of a monogenic disease) in a mixed cell population containing minimal fetal material including as few as one fetal cell in ten cells.

Following sorting, the separated cells can be washed twice in a physiologic buffer and resuspended in an appropriate medium for any subsequent analysis to be performed on the cells.

Post-Recovery Processing

Following the present recovery method, whether based on solid phase or FACS separation, the fetal cells can be used in the same manner as fetal cells obtained by other methods such as amniocentesis and chorionic villus biopsy. The cells can be used as a source of DNA for analysis of the fetal alleles, as by polymerase chain amplification. PCR analysis methods have been used to detect, for example, fetal sex, $\beta$-thalassemia, phenylketonuria (PKU), and Duchenne's muscular dystrophy.

Alternatively, the cells can be cultured in the same manner as biopsy materials for karyotyping analyses. However, the incubation period may be significantly shortened if a DNA content of greater than or equal to 2 C is used as a selection criterion.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense.

EXAMPLE 1

Preparation of Labeled Antibodies

Two monoclonal antibodies specific for two HLA A locus alleles were labeled. The antibody designated GSP 16.1 (Anti-A 1, 9, 10 and 11; IgM monoclonal antibody from Genetic Systems, Seattle, Wash.; 10th International Workshop No. 2004) was labeled with FITC. The antibody designated GSP 20.1 (Anti-A2, w69; IgG monoclonal antibody from Genetic Systems, Seattle, Wash.; 10th International Workshop No. 2021) was labeled with biotin. Cells which reacted with the biotinylated antibody were subsequently reacted with PE-labeled strepavidin. The reagents used to purify and label the antibodies are described below.

Biotinylation Buffer
0.42 gm $Na_2CO_3$
8.06 gm $NaHCO_3$
QS to 1 liter, pH to 8.4
FITC Conjugation Buffer
3.18 gm $Na_2CO_3$
5.86 gm $NaHCO_3$
QS to 1 liter, pH to 9.6
FITC (Sigma Chemical Co., cat. #F-7250)
Stock Solution FITC: Dissolve 10 mg in 1 ml DMSO (dimethylsulfoxide)
Working Solution FITC: Dilute stock to 1 mg/ml in FITC conjugation buffer
Biotin (Molecular Probes, cat. #S-1582)
Stock Solution Biotin: Dissolve 10 mg in 1 ml DMSO
Working Solution Biotin: Dilute stock to 1 mg/ml in DMSO For the IgG antibody (GSP 20.1), the antibody was first purified by column chromatography using a MAB-Trap G Kit (Pharmacia LKB) to remove other proteins, particularly albumin. This kit utilizes Protein G Sepharose 4 Fast Flow Chromatography media. (Use of Protein G Sepharose is equivalent.) The antibody-containing eluate (15 ml) was concentrated in an Amicon B125 concentrator until the final volume was approximately 2.0 ml (approximately four times the original volume). The antibody was removed from the concentrator to a 12×75 mm test tube. The volume was adjusted to exactly 2.5 ml with biotinylation buffer.

The IgM antibody was not pre-purified. A 0.5 ml antibody sample was diluted to 2.5 ml with FITC conjugation buffer.

A PD-10 column from Pharmacia LKB was washed with 25 ml of the appropriate conjugation buffer (FITC conjugation buffer for the FITC-labeled antibody and biotin conjugation buffer for the biotinylated antibody). The 2.5 ml sample of each antibody was applied to the appropriate column. When the column stopped dripping, a 3 ml aliquot of the appropriate conjugation buffer was applied. Each antibody-containing eluate was collected.

Each eluate was concentrated in an Amicon B125 concentrator until the final volume was 1 ml. The antibody was removed from the concentrator and placed in a 1.5 ml microcentrifuge tube. The amount of protein present was assessed using a kit (Protein Assay Kit #2, BioRad, Richmond, Calif.) that utilizes the Bradford method of protein quantitation.

Once the quantity of antibody (the amount of protein) was calculated, the FITC and biotin were added as follows. A 100 μl aliquot of the working solution of FITC per mg of protein was added to the IgM antibody. A 120 μl of working solution of biotin/mg protein was added to the IgG antibody. Each solution was mixed, and each tube was covered with aluminum foil and rocked on a hematology blood rocker overnight at room temperature.

One PD-10 column for each antibody was prepared by running 25 ml of Phosphate Buffered Saline (PBS), pH 7.4 (0.01M phosphate, 0.15M NaCl) through it. Following the incubation, each antibody preparation was diluted to 2.5 ml with PBS and layered over the column. When the column stopped dripping, a 3 ml aliquot of PBS was run through and the eluate was collected.

Each antibody was again concentrated in the Amicon B125 to a final volume of 1 ml. The protein content was again quantitated, and the final concentration was adjusted to 40 μg/ml. In the case of the IgM antibody, the amount of antibody present was estimated to be one-half of the total protein present and was diluted to 40 μg/ml. Bovine serum albumin (BSA) was added to a final concentration of 10 mg/ml and sodium azide was added to a final concentration of 0.1%.

EXAMPLE 2

Preparation of Cells for Labeling

Heparinized whole blood (30 ml) of each sample was layered onto room-temperature Ficoll-Hypaque (Pharmacia-LKB) gradient material at a ratio of 5 ml blood to 3 ml ficoll in separate tubes. The tubes were spun in a swinging bucket centrifuge for 30 minutes at 400 g. The mononuclear layer of each was removed to another tube and washed twice with RPMI 1640 tissue culture media (Mediatech, Inc., Herndon, Va.) with 5% autologous plasma. The samples were then counted on a hemocytometer, adjusted to $5 \times 10^7$/ml in RPMI, then recounted.

EXAMPLE 3

Labeling Cells in a Blood Sample

Labeled antibody is usually used at a concentration of about 2 μg/$10^6$ cells. In this case, 50 μl of the antibody per $10^6$ cells was used for staining. The cells were stained and sorted effectively using that amount of antibody.

The cells ($10^6$ cells in 100 μg of RPMI 1640 tissue culture media plus 5% autologous plasma), prepared as described in Example 2, were stained as described below to assess the conjugation of the label to the antibodies.

Tube #1-No antibody added (negative)
Tube #2-GSP 16.1 (Anti-All, IgM monoclonal antibody) FITC conjugated; 50 μl
Tube #3-GSP 20.1 (Anti-A2, IgG monoclonal antibody) Biotin conjugated; 50 μl
Tube #4-GSP 16.1+GSP 20.1; 50 μl of each The tubes were mixed and incubated in the dark at 4° C. for 30 minutes. After this time, 10 μl of TAGO (Burlingame, Calif.) PE-strepavidin was added to tubes #3 and #4. This reagent reacts with biotin lending to a biotin/avidin-PE complex which allows the biotin-labeled cells to be fluorescent. The cells were incubated an additional 30 minutes after which the cells were washed twice with ice cold PBS and resuspended in 1 ml of PBS.

EXAMPLE 4

Sorting Labeled Cells

Cells which were labeled as described in Example 3 were subjected to flow cytometric analysis using log green fluorescence (FITC) versus log red fluorescence (PE). (The cells were from a donor having the HLA type A2, All.) This results in a plot that is termed a two-dimensional (2D) plot, contour plot (if contours are drawn), dot plot (if dots are used to represent cells present) or cytogram. When the X-axis representing FITC and the Y-axis representing PE fluorescence are plotted against one another, the resulting graph can be divided into four quadrants. Lower left is where the negative or unstained cells fall. Lower right is where the FITC- labeled (green) cells fall. Upper left is where the PE- labeled (red) cells fall. Upper right is where the FITC- and PE-labeled (green and red) cells fall.

This property of cell identification based upon their labeling characteristics as they fall into the various quadrants of the graph was used to locate and subsequently sort out those located cells.

EXAMPLE 5

Dilution Studies to Evaluate Rare Cell Sorting

In these studies, cells from a blood sample from donor A (sample A) were mixed with cells from a blood sample from donor B (sample B) to mimic rare event cell analysis/sorting using a flow cytometer. This series of experiments was performed to evaluate the ability of flow cytometry to not only define but also isolate these rare cells. These studies were performed by diluting blood from two individuals who have one A locus allele in common. In this way, a predetermined number of cells from each individual were known to be present in a sample.

Antigens for GSP 16.1 and GSP 20.1 are both found on the surface of sample A cells. These cells, when reacted with these monoclonal antibodies, had both red and green fluorescence on their surface. Antigen GSP 20.1 is also found on the surface of sample B cells. These cells, when reacted with this monoclonal antibody, had only red fluorescence on their surface. Thus, the labeling patterns mimic the patterns of a pregnant woman and the fetus.

Sample A was mixed into sample B at ratios of 5%, 1%, 0.1% and 0.001%. In the second study, sample A was mixed into sample B at ratios of 1%, 0.1%, 0.001% and 0.0001%. The dilutions of A into B were calculated so that at least 1000 cells of A were present in the test tube.

The cells were labeled according the procedure in Example 3. Monoclonal antibodies GSP 16.1 and GSP 20.1 were both added to each of the tubes of mixed cells using 50 $\mu$l of antibody prepared as described in Example 1 per $10^6$ cells. The cells were vortexed, and the tube was covered with aluminum foil and placed on an ice pack which was mounted on a hematology blood rocking device.

After the antibody incubation, strepavidin-phycoerythrin (TAGO) was added to each tube of biotin-labeled cells using 10 $\mu$l of undiluted PE-strepavidin per $10^6$ cells. The cells were again vortexed and incubated as previously for another 30 minutes.

Following the incubation, the samples were centrifuged at 1000 g for 3 minutes, washed twice with ice cold PBS, resuspended in RPMI to approximately the original volume and placed on ice.

A separate set of three control tubes containing $10^6$ sample A cells only was reacted in the same manner as above with GSP 16.1, with GSP 20.1 and with GSP 16.1 in combination with GSP 20.1. A fourth aliquot of cells was left untreated with monoclonal antibodies. This group of four tubes was used to assess the antibody labeling of the cells in the study, and to set the flow cytometry instrument for color compensation, log amplification offset, signal gains, etc. The fluorescence parameters of the instrument were adjusted to produce four quadrant separation of the cells (as discussed previously).

The lowest dilution tubes were analyzed/sorted first. Because the cells in this study were fresh, treated with mild centrifugation and kept at low temperatures, there was minimal debris and clumping of the cells as evaluated by the 90 degree versus forward light scatter parameter. The cells formed a tight, dense cluster on the display.

Only one region (gate) was defined for sorting. This was an area where the dual-labeled sample A cells would fall on log green versus log red fluorescence parameter display. By defining only one region, the computer had to make one decision in the evaluation of which cells to sort. If the cell fell into the defined gate region of the display, the cell was sorted.

The instrument was set to sort in one drop deflection/purity mode. This means a cell is sorted only if it can confidently be sorted without an unwanted cell being sorted with it. The inclusion of unwanted cells can occur if the cells are located in close proximity to one another resulting in unwanted cells being included in a drop of fluid including wanted cells. This one drop deflection/purity mode lends an added discrimination to the process resulting in a higher percentage of purity in the sorted cells of choice.

The average speed of the sort was approximately 10,000 cells/second. As the cells passed through the instrument, statistics were computed to evaluate the number of cells falling in the sort gate region as well as the number of cells which the instrument sorted.

A collection apparatus for the sorted cells consisted of a 10 ml beaker fitted into a solid support located directly under the sort streams. These beakers are layered with 100 to 200 $\mu$l of approximately 50% autologous plasma in RPMI. This layer helps to cushion the cells when they enter the collection vessel.

After at least 3,000 of the cells which were located in the gated region were sorted, the contents of the beaker was poured into another test tube and resubmitted to the flow cytometer for statistical analysis. This process of evaluating the efficacy of the sorting procedure by analyzing the sorted cells using the instrument is referred to as "playback", "sort playback", or simply, "second pass". The statistics obtained from this evaluation of the sorted cells provides information on the alteration in the percentage of the two cell populations from the original tube due to the sort process. It is from this analysis of the sorted cells that the percentage of purity or enrichment of the sorted population can be evaluated.

Using this process, the study demonstrated that in tubes where sample A was diluted at or greater than 0.01%, the flow cytometer was not able to discriminate the signal of the dual-labeled cells as clearly as with the lower dilution. The cells were discriminated. However, the reliability of detecting only the rare cells starts to diminish. This is attributed to statistical problems related to the instrument whereby stray signals caused by inherent noise in the system due to cell clumps, debris, etc., may be evaluated in the region designated for our rare cells. To overcome this limitation, additional parameters, such as a third fluorescent color, cell size, etc. can be used to locate the rare cells.

The study also demonstrated that in tubes where sample A was diluted at 0.01% and greater, the number of cells which were sorted were less than 3,000. On the playback, the reliability of the analysis was hindered because there were so few cells amidst a pool of noise. This was best seen when an analysis of a playback of a 0.01% dilution tube showed an enrichment of this population to 30%. The next higher dilution tube (0.001%) was sorted directly onto a microscope slide coated with autologous plasma (dry).

Evaluation of the wet mount of this sorted population using a fluorescence microscope revealed nearly 60% of the cells present carried the dual label. Visual inspection revealed a background of dye crystals, debris, etc. which, if played back, would have been picked up by the flow cytometer and counted resulting in what would appear as a lower overall recovery of dual-labeled cells. Less diluted samples are expected to have higher purity than more diluted samples. Therefore, the 0.01% dilution would be expected to have greater than 60% purity.

The evaluation of the dilution-sort studies demonstrated that the present method makes it possible to locate, sort and enrich the diluted cell population appreciably from its original low percentage. In summary, the percentage of sample A cells that were sorted and the percentage of sorted cells, as determined by evaluating the population by FACS is listed below. The evaluation by visual inspection on a slide, as described above, is also shown for a 0.001% dilution.

| (pre-sort) | (post-sort) |
| --- | --- |
| 5% | 75% |
| 1% | 60% |
| 0.1% | 55% |
| 0.01% | 30% |
| 0.001% | 60% (determined visually) |

The limits of discrimination of the number of cells in a gated region using two fluorescence parameters as determined in this study was about 0.01%. Cells falling in this region at higher dilution levels appear to be overestimated.

EXAMPLE 6

Repeat of Dilution Studies

The study described in Example 5 was repeated, including repetition of the monoclonal antibody labeling process. The limits of discrimination in the second study again were at the 0.01% level. The cells from these studies were sorted onto slides coated with plasma and air dried. Approximately 100 cells from dilutions ranging from 1% through 0.0001% were sorted.

EXAMPLE 7

Dilution Studies Using Single-Labeled Rare Cells

Another study was performed as described in Example 6 in which the single-labeled cells were diluted to be the rare cells. (The antibody labeling procedure was not repeated.) Sample A was treated as the maternal, dual-labeled cells and sample B as the fetal, single-labeled cells at dilutions of 0.1, 0.01 and 0.001%. The results obtained were similar to those described in Example 5, above. This demonstrates that the fetal cells can be separated from the maternal cells based upon a single fluorescent label. This more closely mimics the inventive method since the mother antigens can be determined, allowing her cells to be dually labeled. As demonstrated by this study, any combination of the four quadrants where cells can be placed (unstained, red only, green only and red plus green) can be used to separate/sort the cells of interest.

As shown in Examples 5 through 7, a distinction was made between sample A cells and sample B cells based upon fluorescence characteristics following labeling with antibodies for HLA antigens where the labeled cells shared a single antigen of one HLA locus.

EXAMPLE 8

FACS Separation of Rare Cells from Maternal Blood

Blood was drawn from a woman in her ninth week of pregnancy. As in the studies described in Examples 5–7, the mother and father shared a common antigen for the A locus. The mother's other A antigen was A2, which reacts with the GSP 20.1 antibodies. The father's discriminating A antigen reacts with GSP 16.1 antibodies;.

For this study, the maternal GSP 20.1 antibodies were labeled with biotin/PE and the paternal GSP 16.1 antibodies were labeled with FITC as described in Example 1. The blood was purified and stained as described in Examples 2 and 3. For this study, maternal cells were stained red; paternal cells green.

Cells in the maternal blood were predominantly red with rare (fetal) cells labeled with red and green. Out of about $5.5 \times 10^6$ sorted maternal cells, cells retrieved by the red and green sort criteria comprised about 0.1% of the cell population. Of those sorted cells, about 20% were red and green labeled.

The study described above was repeated on samples from the same woman in her tenth and eleventh weeks of pregnancy and provided the same results.

This experiment demonstrates that fetal cells are present in the peripheral blood of a woman in her first trimester of pregnancy, as early as week 9, and can be retrieved from maternal blood using a fluorescent staining pattern that distinguishes maternal and fetal HLA antigens encoded by a single HLA locus.

EXAMPLE 9

Separation of Rare Cells Using Magnetic Beads

Additional samples of the cells used in Example 8 were separated using DYNABEAD magnetic beads (Robbins Scientific, Mountain View, Calif.). The GSP 16.1 antibody (IgM), the fetal HLA A antigen not present on maternal cells, was affixed to the beads by conjugation of the antibody according the manufacturer's directions. This antibody was used due to its availability. This antibody separation functions in the same manner as separations based on binding maternal cells, except that, in this case, the rare, fetal cells are solid phase-affixed and maternal cells are non-bound (rather than maternal cells for the nontransmitted antigen being solid phase-affixed and fetal cells being non-bound as in the inventive method).

The maternal blood cells were purified by ammonium chloride lysis and were suspended in PBS at 4° C. The manufacturer recommends using $1 \times 10^6$ to $1 \times 10^7$ beads per ml and a ratio of about five beads per cell. However, upon consultation, a ratio of about 1 or fewer beads per cell was suggested for applications where cells of choice were removed from a mixture of cells.

An experiment using a ratio of 0.05 and 0.5 beads/cell was performed. The GSP 16.1 antibody was conjugated to the beads ("16.1 beads") and a negative control antibody (GSP 56.1, an antibody for HLA B 27.1, an antigen not present in either parent) was conjugated to a second set of beads ("56.1 beads") to assess non-specific binding. The purified blood cells were incubated with the beads at 4° C. for 60 minutes.

The 16.1 beads using a 0.05 to 1 ratio had too few beads to evaluate. The 16.1 beads using a 0.5 to 1 ratio had readily visible rosettes of cells. The 56.1 beads had a few cells per bead and no prominent rosettes. Cytocentrifugation of the control bead preparation demonstrated that the rosetted cells were mainly monocytes.

To verify the fetal origin of the rosetted cells, the study was repeated using the bead to cell ratio of 0.5. Since the beads were sufficiently large to permit binding of FITC-labeled cells, the blood cells were counterlabeled with FITC-labeled GSP 16.1 antibodies prior to incubation with the beads so that fetal cells were green. The cells were incubated with the beads as described above, except that whenever fluorescent labels were used, the incubation was performed in the dark. Following incubation, the solid phase affixed fetal cells were separated from maternal cells using a magnet and removed from the magnetic beads. The separated fetal cells were placed in RPMI 1640 medium for further analysis.

Analysis of the solid phase-affixed cells showed the cells were green, confirming that the cells were of fetal origin.

The fetus was subsequently determined to be a male. The separated cells were confirmed to be fetal cells by the following procedures. First, the presence of one of the paternal HLA antigens in the enriched "fetal" cell population was confirmed by the fluorescent staining of the cells. That is, the cells were not bound to the beads in a non-specific manner. Second, the presence of the Y chromosome in separated "fetal" cells was confirmed by Y chromosome-specific sequence amplification according to the procedure described in Kogan et al, *New Engl. J. Med.* 317:985–990 (1987).

The presence of the Y chromosome sequences and the presence of one of the paternal HLA antigens demonstrates that the cells were of fetal origin and that the cell preparation was sufficiently enriched for purposes of genetic analysis.

What is claimed is:

1. A method for recovering fetal cells from a blood sample obtained from a pregnant woman having a first cell surface antigen encoded by a first allele of a polymorphic genetic locus and a second, different cell surface antigen encoded by a second allele of a polymorphic genetic locus, said method comprising:
   a. combining cells of said sample with a first antibody specific for said first cell surface antigen for a period of time sufficient for antibody binding;
   b. combining cells of said sample with a second antibody specific for said second cell surface antigen for a period of time sufficient for antibody binding;
   c. separating maternal cells bound to said first antibody and said second antibody from fetal cells which are bound to one antibody or are non-bound; and
   d. recovering said separated fetal cells.

2. The method of claim 1 wherein said first antibody is labeled with a fluorochrome and cells bound to said first antibody are separated from cells which are not bound to said first antibody using fluorescence-activated cell sorting.

3. The method of claim 2 wherein said second antibody is labeled with a second, different fluorochrome, and the same cells are combined with the first antibody and the second antibody to produce double-labeled maternal cells, and double-labeled maternal cells are separated from singled-labeled or unlabeled fetal cells.

4. The method of claim 1 wherein said first antibody is affixed to a solid phase.

5. The method of claim 4 wherein the cells are separately combined with said first antibody and said second antibody.

6. The method of claim 5 wherein said first antibody and said second antibody are separately combined with said cells sequentially.

7. The method of claim 1 wherein said blood sample is purified to remove red blood cells prior to combination with said first antibody.

8. The method of claim 7 wherein said purification is performed using a gradient material having a density intermediate between red blood cells and lymphocytes.

9. The method of claim 7 wherein said purification is performed using a hypotonic solution.

10. The method of claim 1 wherein at least one of said first and said second antibodies is specific for a blood group antigen.

11. The method of claim 1 wherein at least one of said first and said second antibodies is specific for an HLA antigen.

12. The method of claim 1 wherein said first and said second antibodies are specific for cell surface antigens expressed by different alleles of the same polymorphic genetic locus.

13. The method of claim 1 wherein said first and said second antibodies are specific for cell surface antigens expressed by alleles of two different polymorphic genetic loci.

14. A method for recovering fetal cells from a blood sample obtained from a pregnant woman having different first and second cell surface antigens expressed by a first allele of a polymorphic genetic locus and a second allele of a polymorphic genetic locus, said method comprising:
   a. combining the cells of said sample with a first solid phase-affixed first antibody specific for said first antigen for a period of time sufficient for antibody binding;
   b. separately combining the cells of said sample with a second solid phase-affixed second antibody specific for said second antigen for a period of time sufficient for antibody binding;
   c. separating cells bound to each of said solid phases by said first antibody or by said second antibody from any non-bound cells; and
   d. recovering said separated, non-bound cells.

15. The method of claim 14 wherein said solid phases are magnetic beads and solid phase-affixed cells are separated from non-bound cells using a magnet.

16. The method of claim 14 wherein steps (a) and (b) are performed sequentially.

17. A method for recovering fetal cells from a blood sample obtained from a pregnant woman having different first and second antigens expressed by a first and a second allele of an HLA locus, said method comprising:
   a. combining the cells of said sample with a first solid phase-affixed first antibody specific for said first antigen for a period of time sufficient for antibody binding;

b. separately combining the cells of said sample with a second solid phase-affixed second antibody specific for said second antigen for a period of time sufficient for antibody binding;

c. separating cells bound to each of said solid phases by said first antibody or by said second antibody from any non-bound cells; and d. recovering said separated, non-bound cells.

18. The method of claim 17 wherein said HLA locus is selected from the group consisting of A, B, and C.

19. The method of claim 17 wherein said HLA locus is selected from the group consisting of DR, DQ, and DP.

20. The method of claim 17 comprising the additional step of obtaining DNA from said recovered fetal cells.

21. The method of claim 17 comprising the additional step of culturing said recovered fetal cells.

22. The method of claim 17 additionally comprising the step of determining the alleles of said pregnant woman for at least two HLA loci.

23. The method of claim 22 wherein the alleles of said HLA loci are determined using serological methods.

24. The method of claim 22 wherein the alleles of said HLA loci are determined by using DNA analysis methods.

25. A method for obtaining DNA from fetal cells recovered from a blood sample obtained from a pregnant woman having different first and second antigens expressed by a first and a second allele of an HLA locus, said method comprising:

a. combining the cells of said sample with a first antibody specific for said first antigen and labeled with a first fluorochrome and with a second antibody specific for said second antigen and labeled with a second, different fluorochrome for a period of time sufficient for antibody binding to produce a sample containing labeled cells;

b. separating double-labeled cells of said sample from single-labeled cells using fluorescence-activated cell sorting to produce separated, single-labeled cells;

c. recovering said separated, single-labeled cells; and d. obtaining DNA from said recovered fetal cells.

26. A method for recovering and culturing fetal cells from a blood sample obtained from a pregnant woman having different first and second antigens expressed by a first and a second allele of an HLA locus, said method comprising:

a. combining the cells of said sample with a first antibody specific for said first antigen and labeled with a first fluorochrome and with a second antibody specific for said second antigen and labeled with a second, different fluorochrome for a period of time sufficient for antibody binding to produce a sample containing labeled cells;

b. separating double-labeled cells of said sample from single-labeled cells using fluorescence-activated cell sorting to produce separated, single-labeled cells; and c. recovering said separated, single-labeled cells; and d. culturing said recovered fetal cells.

* * * * *